(12) United States Patent
Kalpin et al.

(10) Patent No.: US 8,920,389 B2
(45) Date of Patent: Dec. 30, 2014

(54) DETECTING NEEDLE ENTRY INTO A PORT OF AN INFUSION DEVICE

(75) Inventors: Scott L. Kalpin, Harris, MN (US); Scott A. Sarkinen, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 887 days.

(21) Appl. No.: 13/083,731

(22) Filed: Apr. 11, 2011

(65) Prior Publication Data
US 2011/0184354 A1 Jul. 28, 2011

Related U.S. Application Data

(62) Division of application No. 11/693,341, filed on Mar. 29, 2007, now Pat. No. 7,942,863.

(51) Int. Cl.
| | |
|---|---|
| *A61M 31/00* | (2006.01) |
| *A61M 37/00* | (2006.01) |
| *A61B 17/34* | (2006.01) |
| *A61M 5/142* | (2006.01) |
| *A61M 39/02* | (2006.01) |
| *A61M 5/42* | (2006.01) |
| *A61M 5/168* | (2006.01) |
| *A61B 19/00* | (2006.01) |

(52) U.S. Cl.
CPC .... *A61B 17/3403* (2013.01); *A61M 2039/0244* (2013.01); *A61M 2205/3331* (2013.01); *A61M 5/427* (2013.01); *A61M 5/14276* (2013.01); *A61M 2209/045* (2013.01); *A61M 5/16831* (2013.01); *A61B 2019/464* (2013.01)
USPC ................... 604/288.02; 604/288.01

(58) Field of Classification Search
CPC ............ A61M 5/427; A61M 5/14276; A61M 5/16831; A61M 2205/3331; A61M 2209/045; A61B 17/3403; A61B 2019/464
USPC ............. 604/93.01, 115–118, 174, 175, 604/288.01–288.04, 890.1–892.1
See application file for complete search history.

(56) References Cited

U.S. PATENT DOCUMENTS

| | | | |
|---|---|---|---|
| 4,557,722 A | 12/1985 | Harris |
| 4,573,994 A | 3/1986 | Fischell |
| 4,760,837 A | 8/1988 | Petit |
| 4,804,054 A | 2/1989 | Howson |
| 5,006,115 A | 4/1991 | McDonald |

(Continued)

FOREIGN PATENT DOCUMENTS

| | | |
|---|---|---|
| EP | 1 649 884 | 4/2006 |
| EP | 1 832 254 | 9/2007 |

(Continued)

OTHER PUBLICATIONS

PCT Search Report dated Jun. 18, 2008.

*Primary Examiner* — Nathan R Price
(74) *Attorney, Agent, or Firm* — Mueting, Raasch & Gebhardt, P.A.

(57) ABSTRACT

Systems for detecting needle insertion into a port chamber of an implantable medical device include a pressure sensor. The system detects characteristic pressure profiles associated with needle insertion into the port chamber through a septum and may generate a sensory cue to a clinician that proper needle placement has been achieved. Methods for detecting needle insertion into a port chamber of an implantable medical device includes detecting characteristic pressure profiles associated with needle insertion into the port chamber through a septum.

12 Claims, 15 Drawing Sheets

(56) References Cited

U.S. PATENT DOCUMENTS

| | | |
|---|---|---|
| 5,009,644 A | 4/1991 | McDonald |
| 5,171,228 A | 12/1992 | McDonald |
| 5,201,715 A | 4/1993 | Masters |
| 5,507,737 A | 4/1996 | Palmskog |
| 5,957,890 A | 9/1999 | Mann |
| 6,740,076 B2 | 5/2004 | Hoben |
| 6,962,580 B2 * | 11/2005 | Adams et al. ............... 604/891.1 |
| 2004/0073196 A1 | 4/2004 | Adams |
| 2004/0249336 A1 | 12/2004 | Faries, Jr. |
| 2005/0075624 A1 * | 4/2005 | Miesel .......................... 604/505 |
| 2005/0187515 A1 | 8/2005 | Varrichio |
| 2006/0089619 A1 | 4/2006 | Ginggen |
| 2007/0239381 A1 | 10/2007 | Ginggen |

FOREIGN PATENT DOCUMENTS

| | | |
|---|---|---|
| WO | WO 2005/002123 | 5/1985 |
| WO | WO 97/25081 | 7/1997 |
| WO | WO 2007/041471 | 4/2007 |

* cited by examiner

DETECTING NEEDLE ENTRY INTO A PORT OF AN INFUSION DEVICE

RELATED APPLICATION

This application is a division of Ser. No. 11/693,341 filed Mar. 29, 2007 entitled "Detecting Needle Entry Into a Port of an Infusion Device". The entire disclosure of application Ser. No. 11/693,341 is incorporated herein by reference.

FIELD

This disclosure relates, inter alia, to implantable medical devices for delivering fluid to or withdrawing fluid from a target site within a patient. More particularly, it relates to systems, devices and methods for sensing insertion of a needle into a port assembly provided with an implantable medical device.

BACKGROUND

A variety of implantable infusion devices are available for treating patients. For example, implantable infusion devices are used for delivering therapeutic substances to a target location of a patient. The implantable infusion devices are typically implanted subcutaneously in a convenient location in the patient. An infusion catheter is typically connected to an outlet of the device and positioned in the patient to allow delivery to the target location. A therapeutic substance is then typically introduced percutaneously into the implanted device by inserting a needle into a port assembly of the device and delivering a fluid containing the therapeutic substance to the device via the needle.

Because the device is implanted within the patient and cannot be seen directly, care must be taken to ensure that the needle is properly placed into the port assembly before transferring liquids. If the needle is not located within the fill port assembly, delivery of the infusion media through the needle can result failure to adequately treat the patient and potentially dire consequences.

Accordingly, efforts have been made to identify to the clinician a location of the fill port assembly relative to the patient's skin prior to insertion of the needle. For example, templates are well known, and can provide a general indication or map of the port assembly location following palpating the device's periphery through the patient's skin. Additionally, electronic and/or magnetic systems have been suggested that provide the clinician with additional information generally indicative of the port assembly position. Regardless of how the clinician arrives at an initial estimation of port assembly location, upon inserting the needle through the patient's skin, the clinician normally must make a manual/tactile determination as to whether the needle tip has been correctly directed to the appropriate port assembly and has subsequently pierced through a septum covering the port assembly. Most clinician's are relatively comfortable in making this determination as, based on experience, the clinician can tactilely sense or feel when the needle has been inserted through the septum. However, it is sometimes difficult to know with certainty whether the septum has been accessed, especially with thick-skinned patients. Further, as implantable therapeutic substance devices become increasingly reduced in size, the attendant tactile feedback will diminish.

In light of the above, a need exists for a sensor capable of detecting needle presence in a port assembly of an implantable therapeutic substance delivery device. In addition, an indicator device for providing the clinician with a confirmation of desired needle positioning relative to the fill port may be desirable.

SUMMARY

The present disclosure describes, inter alia, systems, devices and methods that can be used to detect needle entry into a port of an implantable infusion device. The methods, systems and devices may be used to detect needle entry by sensing information relating to pressure in a port chamber.

In an embodiment, a method for detecting insertion into a port chamber of an implantable infusion device is described. The device includes a port assembly defining the port chamber. The port assembly includes a septum disposed across an opening of the port chamber to fluidly seal the port chamber relative to an exterior of the device. The method includes sensing a pressure change in the port chamber and determining whether the sensed pressure change is indicative of insertion of the needle through the septum into the port chamber.

In an embodiment, an implantable infusion device is described. The device includes a housing and a port assembly defining a port chamber. The port assembly includes a septum disposed across an opening of the chamber to fluidly seal the port chamber relative to an exterior of the housing. The port assembly is disposed in the housing such that the chamber is accessible by a needle through the opening and the septum from the exterior of the housing. The device further includes a pressure sensor in fluid communication with the port chamber, and includes electronics disposed in the housing and operably coupled to the pressure sensor. The electronics include a computer readable medium containing instructions that when implemented cause the device to detect, via the pressure sensor, a transient pressure increase in the port chamber associated with insertion of a needle into the port chamber.

In an embodiment, a method is described. The method includes inserting a needle through a septum and into a port chamber defined by a port assembly of an infusion device. The septum is disposed across an opening of the port chamber to fluidly seal the port chamber relative to an exterior of the device. The method further includes (i) sensing a pressure change in a port chamber; (ii) determining whether the sensed pressure change is indicative of insertion of the needle through the septum into the port chamber; and (iii) providing a sensory cue if the sensed pressure change is indicative of insertion of the needle through the septum into the port chamber.

By providing devices, systems and methods that allow for detection of needle entry into a port assembly of an implantable infusion device prior to fluid being injected, feedback may be provided to prevent accidental subcutaneous delivery, as opposed to delivery into the device, of therapeutic substance. In instances where the implantable infusion device includes a large reservoir and needle entry into the port assembly is for the purposes of refilling the reservoir, accidental subcutaneous delivery of large quantities of therapeutic substances may result in dire consequences. In cases where the implantable infusion devices contain access ports intended to deliver boluses of therapeutic substances to a target location in a patient, accidental subcutaneous administration of the therapeutic substance will likely fail to result in adequate treatment of the patient. In either case, the ability to detect needle entry into the port assembly prior to infusion of any therapeutic substance through the needle should reduce the likelihood of accidental subcutaneous delivery. Further, use of a pressure sensor to detect needle entry may prove to be advantageous. For example, the pressure sensor may also be used to monitor and confirm proper fluid delivery via the needle into the device to verify that little or no subcutaneous leakage is occurring as a result of fluid delivery. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "sensory cue" means a cue capable of being received by a person, such as an audible, tactile, or visual cue. A visual cue may include, for example, text or an image.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that can be used to detect needle entry into a port of an implantable infusion device. The methods, systems and devices may be used to detect needle entry by sensing information relating to pressure in a port chamber defined by a port assembly. As discussed herein, it has been discovered that a transient increase in pressure can be detected upon needle entry into a chamber of a port assembly of an implantable infusion device upon piercing of a septum disposed across an opening into the chamber, allowing for detection of needle entry into the chamber prior to dispensing fluid from the needle.

Figure 1:
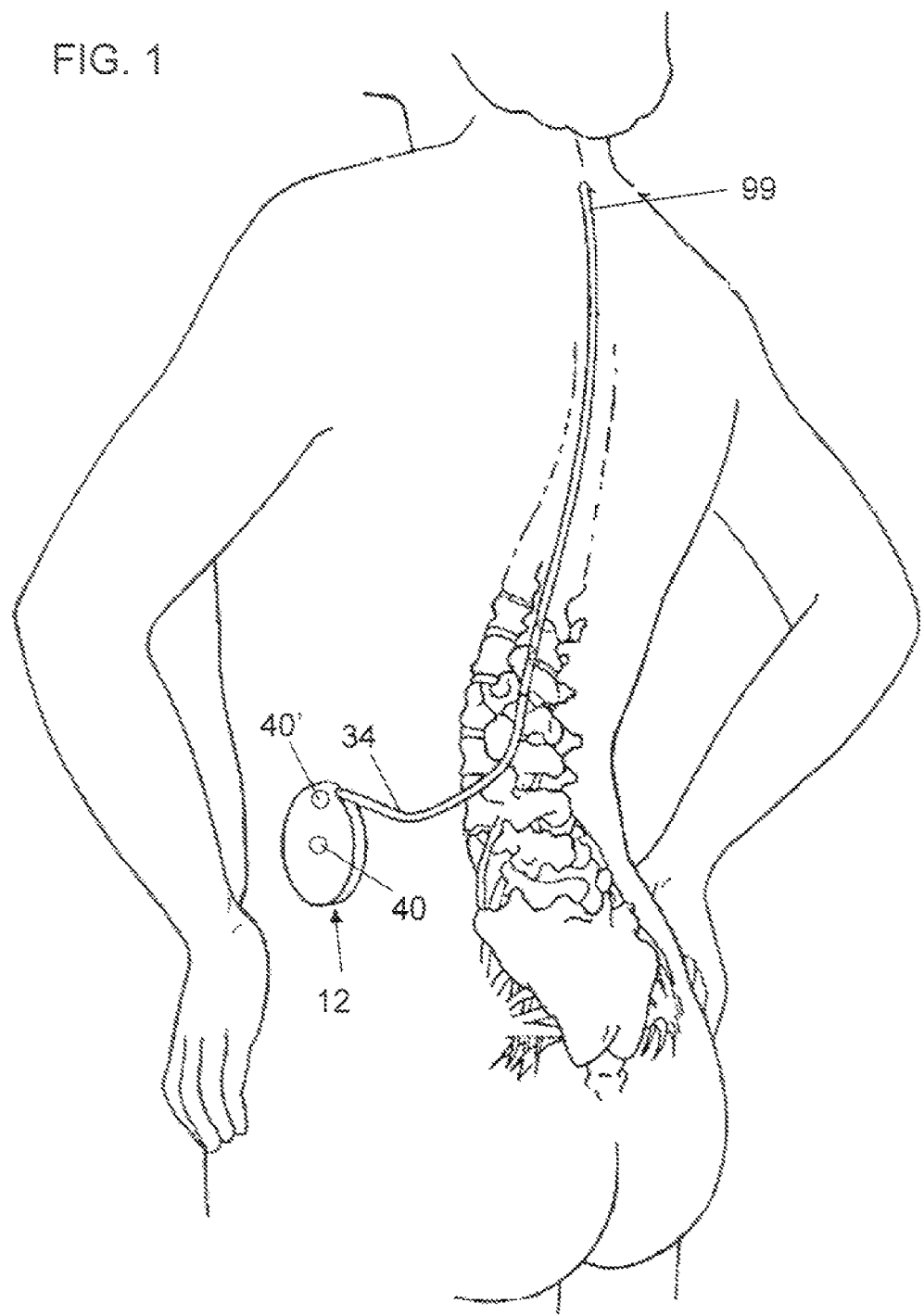
FIG. 1 is a diagrammatic representation of a perspective view of an implantable infusion system implanted in a patient.

Referring to FIG. 1, an implantable infusion device 12 having two port assemblies 40, 40' is shown implanted in a patient. Of course, infusion device 12 may include one, two, three, or any number of port assemblies. As shown in FIG. 1, a catheter 34 is connected to infusion device 12. Distal portion 99 of catheter 12, which may have one or more openings through which fluid may flow, is positioned at or near a target location of patient to deliver fluid from infusion device 12 to target location. The target area depicted in FIG. 1 is the patient's spinal canal. However, it will be understood that any region of a patient's body may serve as a target area depending on the conditions, disease, or disorder to be treated. Port assemblies 40, 40' can be accessed percutaneously by a needle (not shown in FIG. 1), through which fluid may be delivered to infusion device 12.

Infusion device 12 may be any device capable of delivering fluid to a patient. For example, infusion device 12 may be an access port, e.g. a vascular access port, through which bolus injections from needle (not shown) are nearly immediately delivered through a catheter to a patient, or may be a device having a reservoir (not shown in FIG. 1) for holding solutions containing therapeutic substance to be delivered over a period of time, such as devices containing fixed or variable rate pumps, programmable pumps, or the like. Infusion devices having a reservoir will generally include a port assembly to allow for refilling of the reservoir.

The infusion device 12 shown in FIG. 1 has two port assemblies 40, 40' one of which may be a catheter access port and one of which may be a refill port. One exemplary device having a catheter access port and a refill port is Medtronic's SynchroMed® II implantable infusion device. Of course, virtually any other currently known or future developed implantable infusion device can also be used in connection with principles described herein.

While the discussion presented herein is primarily directed to infusion devices for delivering therapeutic substances to a patient, it will be recognized that the principles described herein may be advantageously applied to devices having port assemblies for the withdrawal of fluid from a patient.

Figure 2:
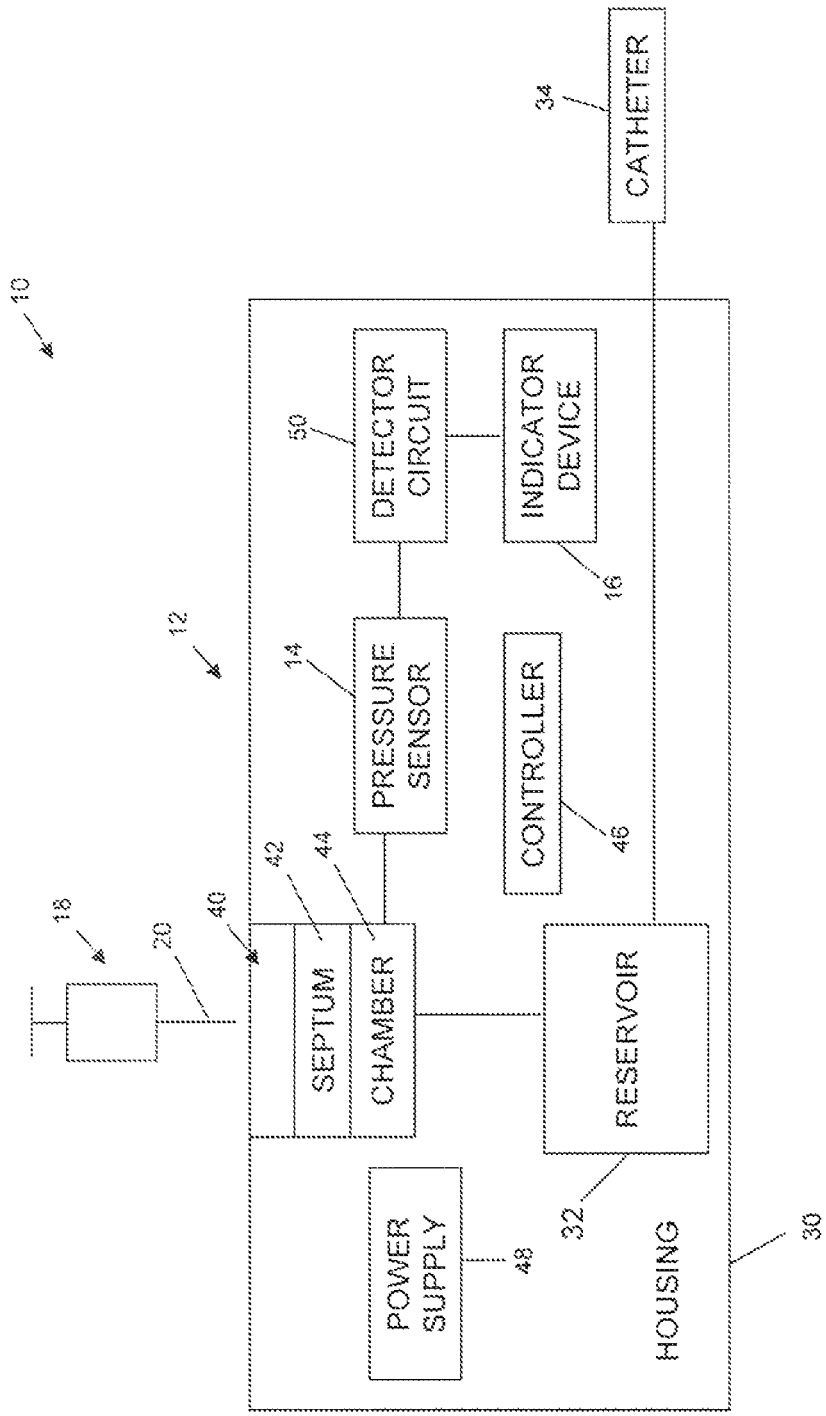
FIGS. 2-8 are block diagrams depicting implantable infusion systems or components thereof in accordance with principles of the teachings herein.

Referring to FIGS. 2-8B, various embodiments of systems and components thereof are shown in block form. FIG. 2 refers to a representative system 10 that includes an implantable infusion device 12, a pressure sensor 14, and an indicator device 16. Also depicted in FIG. 2 is a syringe assembly 18 including a needle 20 useful for percutaneously interfacing with the implantable infusion device 12. In general terms, delivery device 12 shown in FIG. 2 includes a housing 30 that maintains a reservoir 32. Reservoir 32 contains therapeutic substance (not shown) to be delivered to the patient, for example, via a catheter 34. The therapeutic substance can be any infusion agent, product, or substance intended to have a therapeutic effect such as pharmaceutical compositions, genetic materials, biologics, and others (e.g., insulin, saline solution, fluoroscopy agents, etc.). Regardless, a pump and/or metering device (or "flow regulator") (not shown) can be provided for dictating a flow of the therapeutic substance from reservoir 32 in a desired fashion. The pump/metering device can assume a variety of forms, and device 12 can further include a propellant chamber (not shown) associated with reservoir 32 for exerting a constant, positive pressure onto the contained therapeutic substance to ensure delivery to the outlet catheter 34. In other embodiments, the pump/metering device can be eliminated. Regardless, infusion device 12 includes a fill port assembly 40 fluidly connected to, and otherwise defining an inlet of, reservoir 32. In more general terms, however, fill port assembly 40 can assume a conventional configuration whereby a septum 42 seals a port chamber 44 relative to an exterior of the housing 30. Port chamber 44, in turn, is in fluid communication with reservoir 32 (e.g., permanent fluid connection is established, a valve means is provided that actuates to selectively fluidly connect port chamber 44 and reservoir 32, etc.). With this configuration, then, needle 20 can percutaneously deliver a liquid to reservoir 32 upon insertion into fill port assembly 40, and in particular through septum 42 and into port chamber 44, such as part of a reservoir refilling operation.

Figure 3:
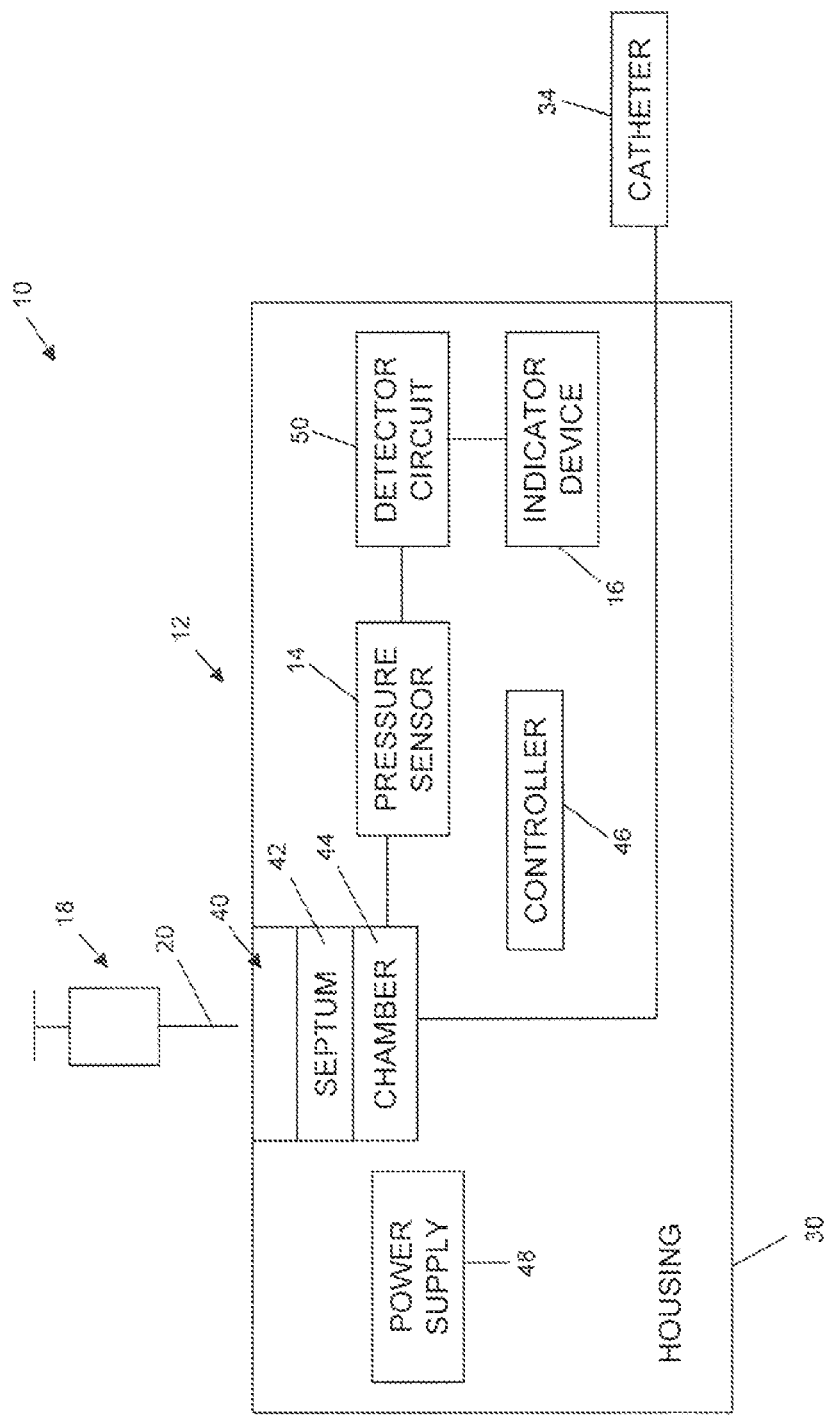

Referring to FIG. 3, an infusion device 12 without a reservoir is shown. In the embodiment shown in FIG. 3, as with the embodiment depicted in FIG. 2, port chamber 44, defined by port assembly 40, is accessible by needle 20 through septum 42. Port chamber 44 is in fluid communication with catheter 34 such that therapeutic infused through needle 20 into port chamber 44 will be delivered to a target area of a patient through catheter 34.

Regardless of the embodiment depicted, infusion device 12 may include additional components as known conventionally or developed in the future. For example, infusion device 12 can include a controller or electronics 46, for example in the form of a digital microprocessor, although any equivalent device may be substituted for a digital microprocessor; in many instances, it may also be desirable that the controller 46 includes data storage capabilities. Where provided, the controller 46 (as well as other components) can be powered by a power supply 48 (that may be preferably be the form of a battery or other self-contained power source). Other components can further be provided with infusion device 12 that are not otherwise illustrated, such as safety valves, flow restrictors, etc., that may enhance operation of the infusion device 12.

With the above general construction of the infusion device 12 in mind, a pressure sensor 14 is maintained by housing 30, and is associated with port assembly 40, reservoir 32 (see, e.g., FIG. 4), or any location at which a pressure change in port chamber 44 can be detected by pressure sensor 14; e.g. in fluid communication with port chamber 44. In various embodiments, and as described in greater detail below, pressure sensor 14 is positioned adjacent or within the port chamber 44 of the port assembly 40. In various embodiments, pressure sensor 14 signals sensed pressure-related information to a detector circuit 50 that in turn may prompt operation of an indicator device 16. As depicted in the embodiments shown in FIGS. 2-4, detector circuit 50 and indicator device 16 are maintained by housing 30. Detector circuit 50 may be adapted or programmed to prompt operation of indicator device 16 based upon pressure-related information generated and signaled by pressure sensor 14. For example, detector circuit 50 can be configured or programmed to prompt operation of indicator device 16 upon determining (e.g., a logic circuit, a comparator, etc.) that the pressure sensed by the pressure sensor 14 (or as otherwise indicated by information signaled from the pressure sensor 14) is indicative of a needle 20 being inserted through septum 42 and into port chamber 44. In the embodiments shown in FIGS. 2-4, detector circuit 50 is shown as being a component apart from controller 46. In other embodiments, however, detector circuit 50 can be provided with the controller 46 such that the controller 46 is programmed to operate indicator device 16 in a desired fashion. In yet other alternative embodiments, detector circuit 50 can be eliminated.

Figure 4:
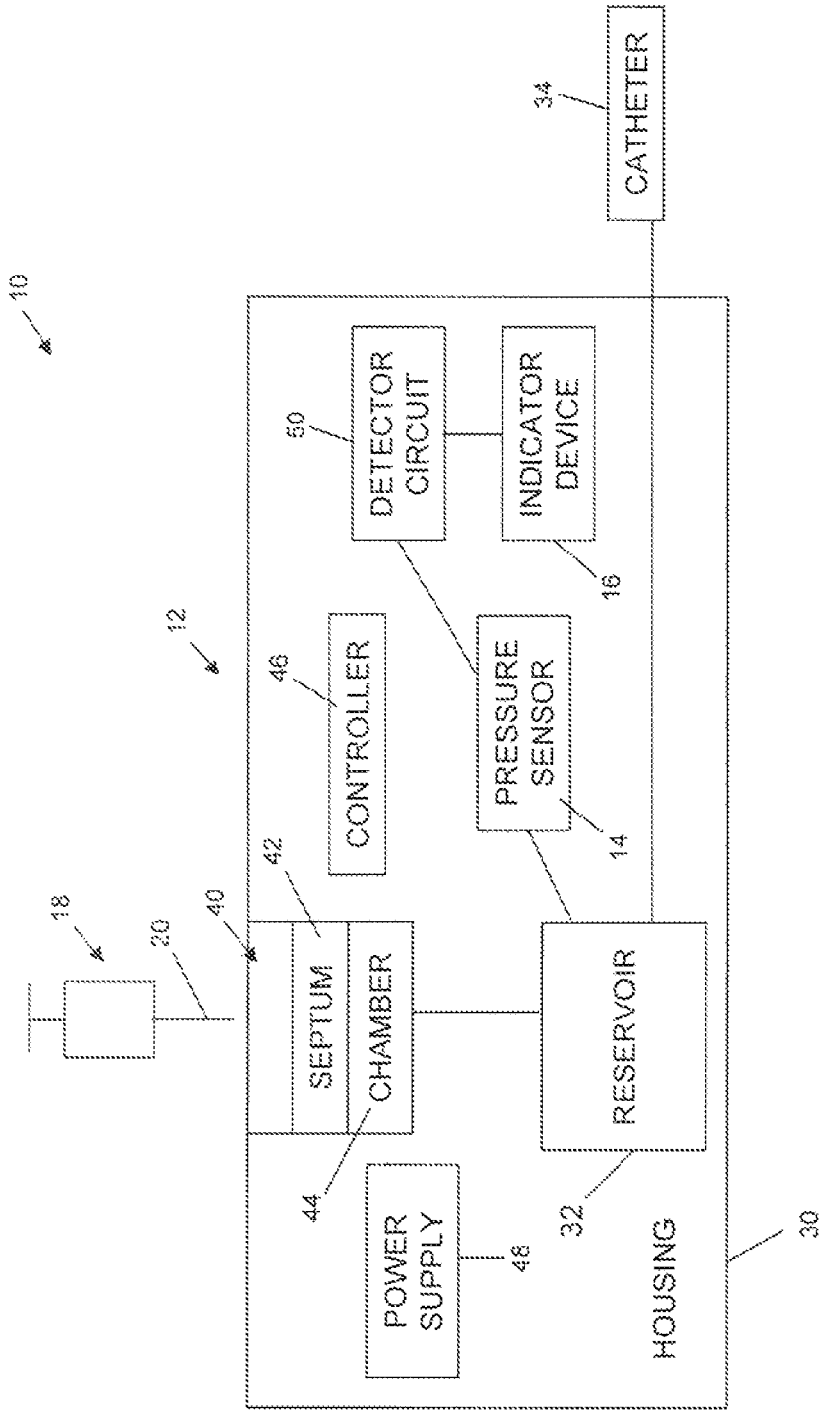

Regardless of whether indicator device 16 is acted upon by a circuit or controller apart from pressure sensor 14, with the embodiments depicted in FIGS. 2-4, indicator device 16 is capable of producing a sensory cue to indicate that needle 20 has entered chamber 44. For example, indicator device may produce an audible noise (e.g., constant or pulsating tones, buzzer-like noise, etc.) at a frequency and decibel level sufficient to be audibly perceived by a clinician otherwise interfacing with delivery device 12 through the patient's skin.

Figure 5:
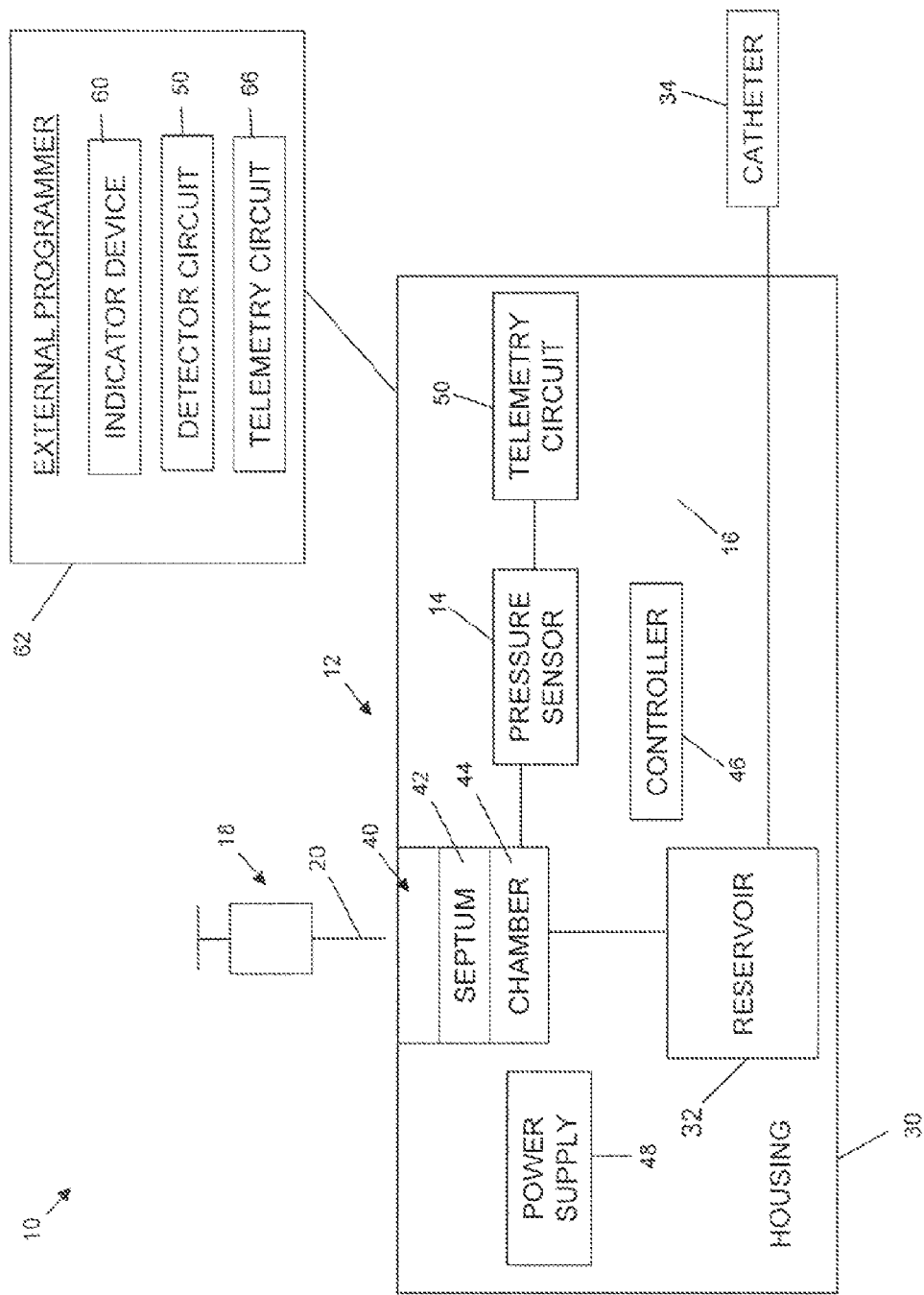

While indicator device 16 has been described as being maintained by the housing 30, in alternative embodiments, indicator device 16 can be provided apart from the housing 30 or a second indicator device (not shown) can be provided external delivery device 12. For example, FIG. 5 is a block diagram representing a representative system 10 that is similar in many respects to the system 10 depicted in FIG. 2. For example, system 10 as depicted in FIG. 5 includes an implantable infusion device 12 otherwise having a reservoir 32 fluidly connected to a port assembly 40. Further, system 10 as depicted in FIG. 5 includes a pressure sensor 14 that is otherwise associated with the port assembly 40 as previously described. In addition, system 10 depicted in FIG. 5 includes an indicator device 60. However, with the embodiment depicted in FIG. 5, indicator device 60 is located apart from housing 30, for example as part of an external programmer 62. External programmer 62 is adapted to communicate with infusion device 12 through the patient's skin such that in various embodiments, external programmer 62 and infusion device 12 are in wireless communication, for example, via telemetry circuitry 64 maintained by the housing 30 and corresponding telemetry circuitry 66 maintained by the external programmer 62 (or a component (e.g., a hand-held instrument) electronically coupled to external programmer 62). Alternatively, other forms of wireless communicative links between infusion device 12 and external programmer 62 can be provided.

Regardless, in various embodiments, pressure sensor 14 is electronically coupled to telemetry circuitry 64 (for example, via a controller (not shown)), with pressure-related information generated by pressure sensor 14 being signaled to external programmer 62 via telemetry circuitries 64, 66. External programmer 62 includes detector circuit 50 previously described (that can be provided as part of a controller associated with the external programmer 62) that dictates operation of indicator device 60. The parameters under which detector circuit 50 will prompt operation of the indicator device 60 are described in greater detail below. In one embodiment, indicator device 60 is a display screen adapted to display information to the clinician. As is known in the art, a display screen is commonly provided with external programmer 62 (e.g., an N'Vision™ Programmer available from Medtronic, Inc., of Minneapolis, Minn. as part of the SynchroMed® II Infusion System), and can display information in a variety of fashions, for example, with text, pictures, symbols, graphical information, etc. Indicator device 60 can further include a sensory cue generator, such as sound generator, as previously described. Regardless, in one embodiment, upon determining that pressure-related information generated by pressure sensor 14 is indicative of needle 20 entering port chamber 44, detector circuit 50 prompts indicator device 60 to inform the clinician via the display screen, sound generating device, or the like. In other embodiments, detector circuit 50 can be eliminated with indicator device 60 simply displaying a current pressure reading provided by the pressure sensor 14. Under these conditions, the clinician can make a self-evaluation as to whether the sensed and displayed pressure is indicative of desired needle placement.

Figure 6:
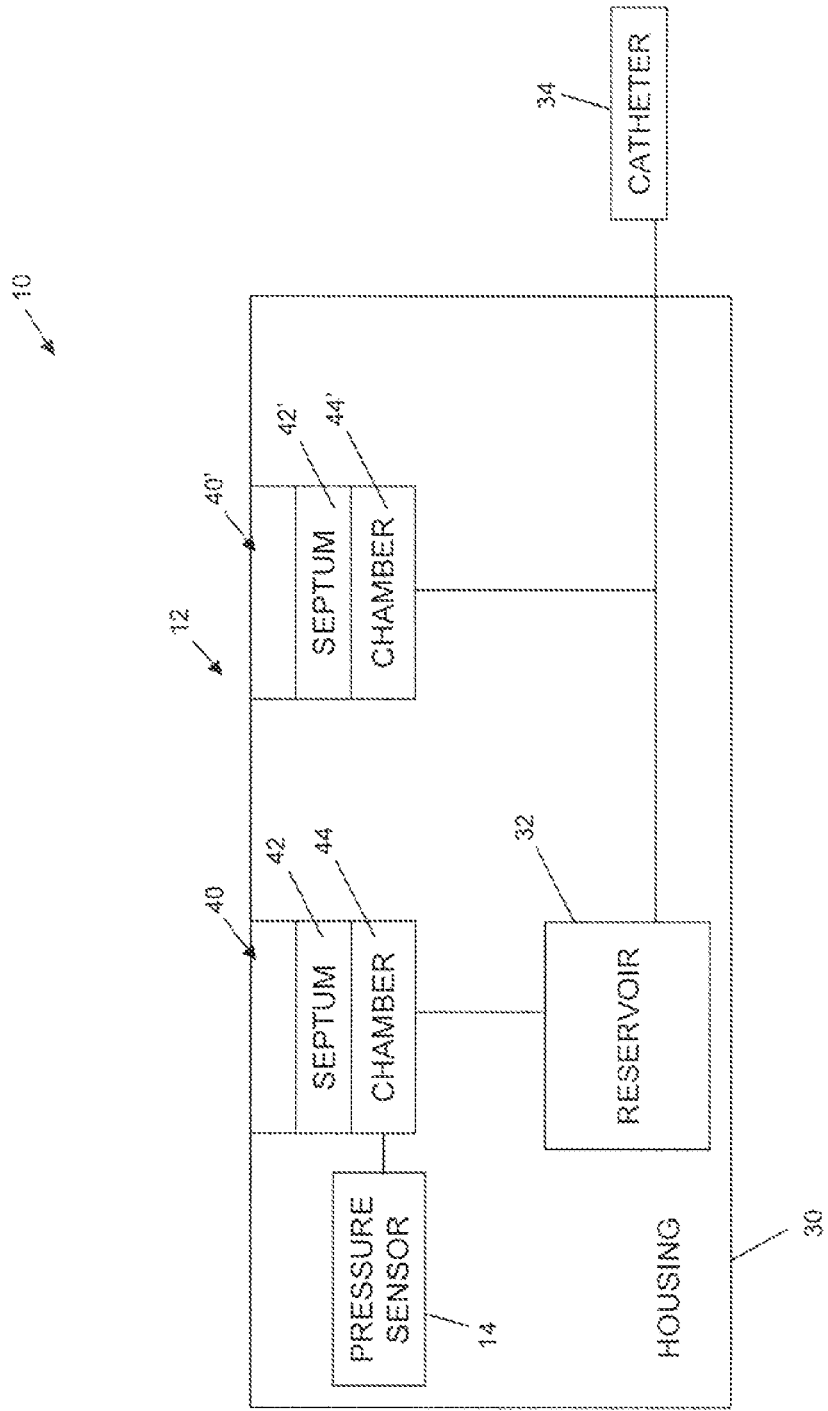
Figure 7:
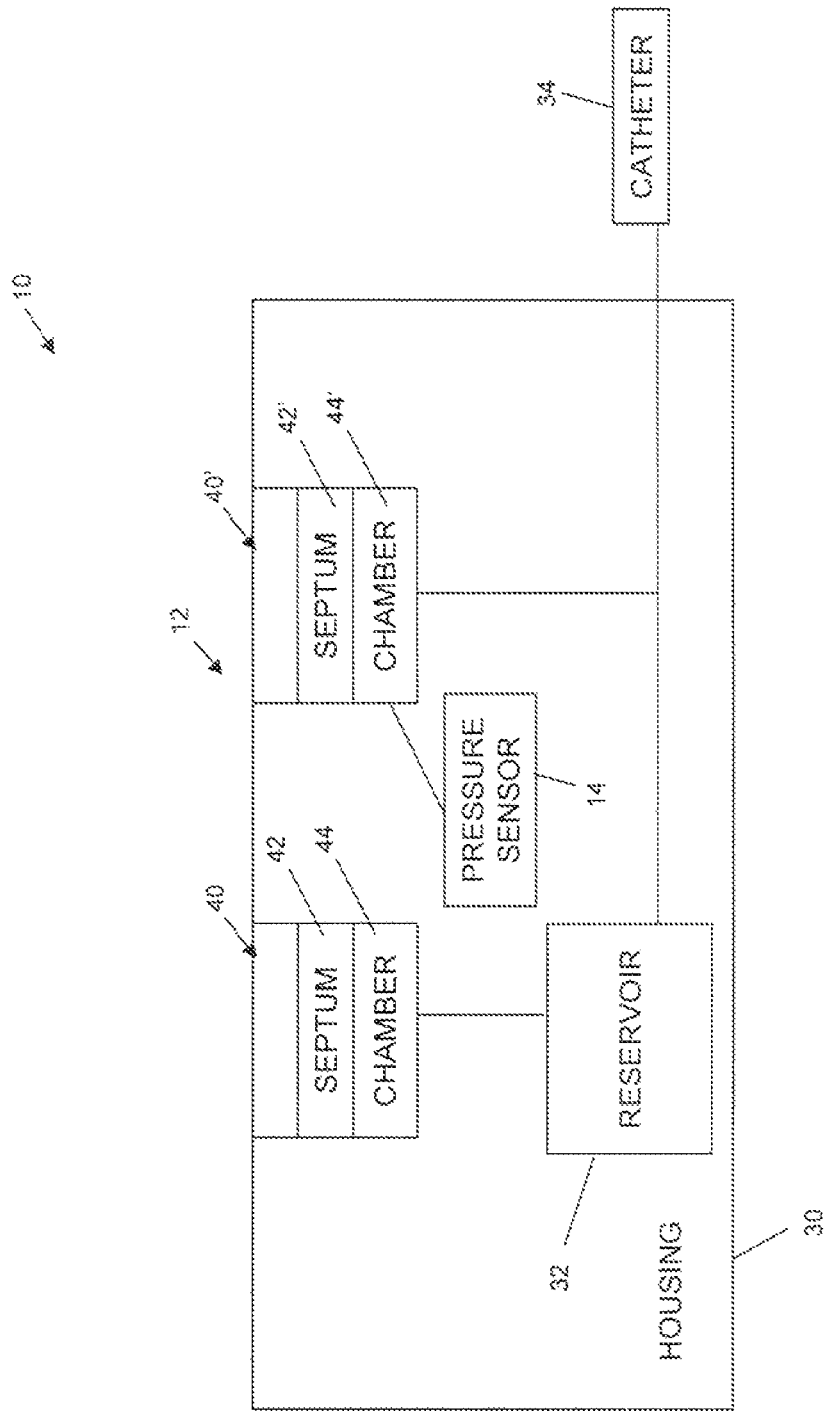
Figure 8:
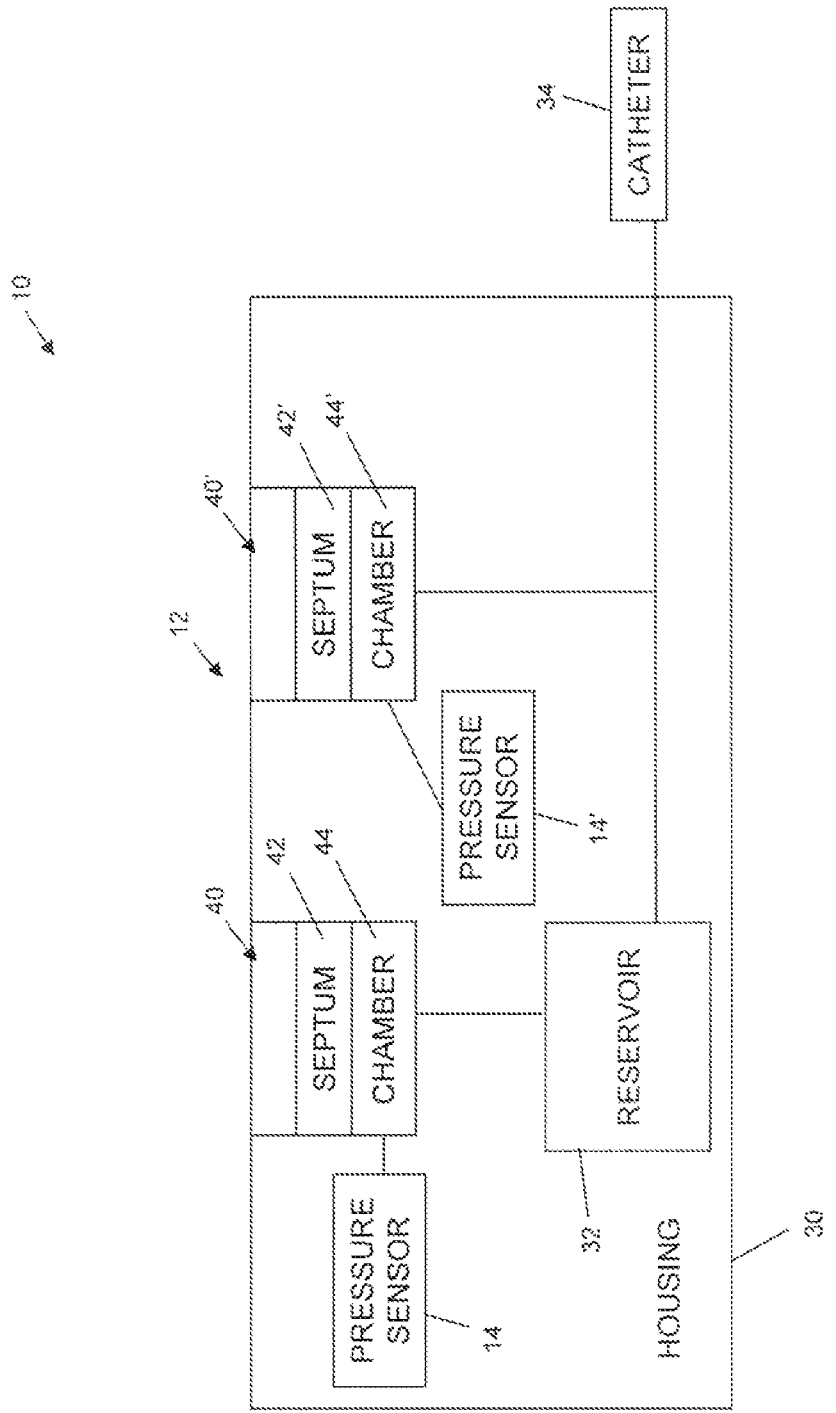

With the above description in mind, FIGS. 6-8 show alternative embodiments of systems 10 in block form. While FIGS. 6-8 do not show some of the features of the devices described in FIGS. 2-5, it will be understood that one or more of the features discussed above may be included. System 10 as shown in FIGS. 6-8 includes two port assemblies 40, 40'. Port assembly 40 is a refill port assembly in fluid communication with reservoir 32, and port assembly 40' is a catheter access port assembly in fluid communication with catheter 34. Pressure sensor 14, 14' may be in fluid communication with fill port chamber 44 (FIG. 6), catheter access port chamber 44' (FIG. 7), or both (FIG. 8). As discussed above, pressure sensor 14 may be positioned anywhere that pressure changes in a chamber 44, 44' can be detected by sensor 14, 14'.

Figure 9:
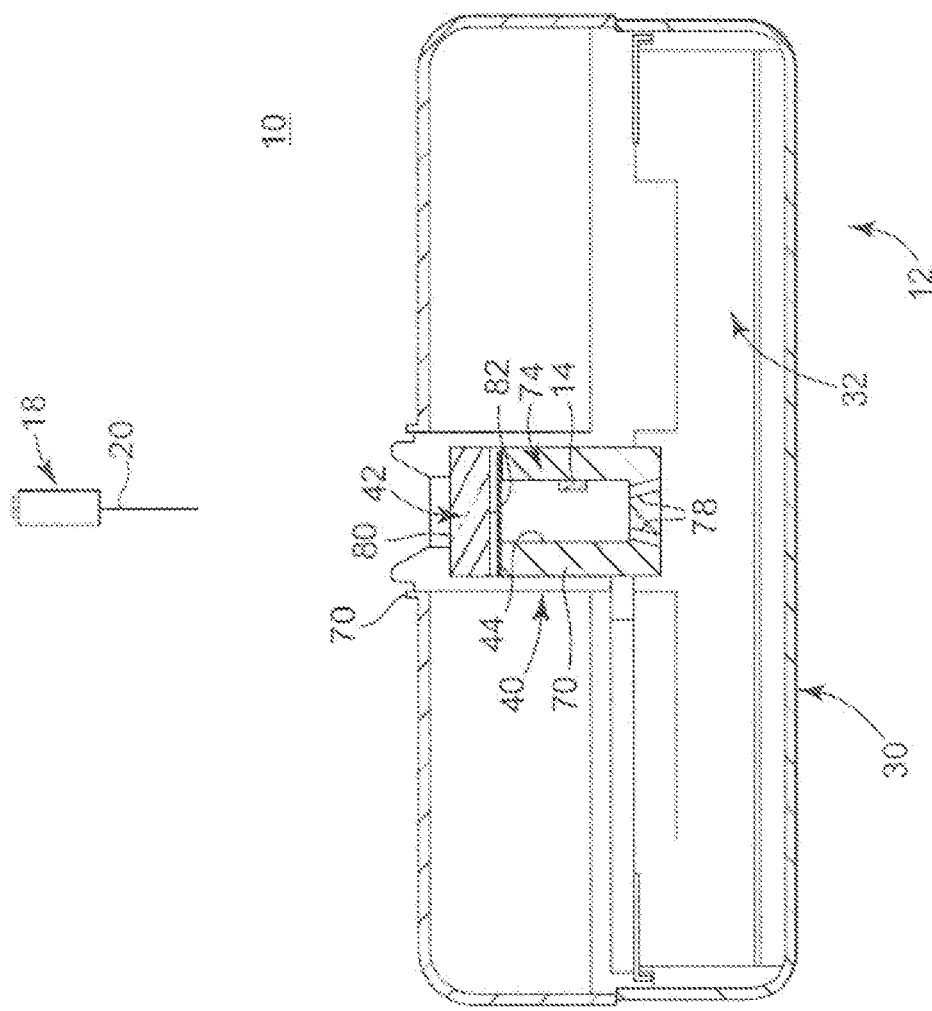
FIG. 9 is a cross-sectional view of a portion of an implantable infusion device useful with the systems of FIGS. 2-8.

FIG. 9 is a simplified, cross-sectional view of an embodiment of a portion of system 10, such as the pressure sensor 14 in conjunction with relevant portions of the infusion device 12, such as housing 30, reservoir 32, and the port assembly 40. In general terms, port assembly 40 is formed in an opening 70 of housing 30 such that port assembly 40 is exteriorly accessible relative to housing 30. Septum 42 is disposed across port chamber 44 (referenced generally) defined by a wall of port assembly 40, such that septum 42 seals the opening 70 relative to the port chamber 44/reservoir 32. Septum 42 can be manufactured of any suitable material or materials. Typically, septum 42 will be made of elastomeric materials, for example, silicone rubber, that are pierceable by needle 20 (which itself does not necessarily form a part of the system 10) and compatible with the therapeutic substance (not shown) to be contained with reservoir 32.

In various embodiments, port assembly 40 further includes a septum plug 74 used to retain septum 42 while providing a fluid-tight seal. Septum plug 74 defines the port chamber 44 to include drain holes 78 that allow fluids delivered to port chamber 44 to pass into reservoir 32. In some embodiments, a valve feature (not shown) can be provided to further control flow of liquid from port chamber 44 to reservoir 32 as is known in the art. As a point of reference, relative to an arrangement of port assembly 40, septum 42 defines a first or exterior side and a second or interior side 82. Exterior side 80 is exposed relative to opening 70 of housing 30, whereas interior side 82 defines a portion of port chamber 44. While FIG. 9 is described with regard to a fill port assembly 40, it will be understood the components described with regard to FIG. 9 can be readily applied or adapted to the catheter access port assembly.

With the above conventions in mind, pressure sensor 14 is, in various embodiments, associated with port assembly 40, and in particular port chamber 44, by disposing the pressure sensor 14 along an interior of a wall of septum plug 74. In other embodiments, pressure sensor 14 is disposed within a thickness of septum plug 74 (such as by forming (e.g., overmolding) septum plug 74 about pressure sensor 14). Even further, pressure sensor 14 can be assembled to an exterior of septum plug 74 (relative to the port chamber 44).

Regardless of an exact location, pressure sensor 14 can assume a variety of different forms. For example, pressure sensor 14 can be a capacitive measurement device which determines pressure by measuring the change in capacitance of a flexible membrane attached but insulated from a conductive, gas-filled cavity due to deflections caused by pressure applied over the flexible membrane. Alternatively, pressure sensor 14 can be a sensor that utilizes the piezo-electric effect or resistive change due to metallic strain in order to measure pressure applied. Regardless, in various embodiments, pressure sensor 14 is adapted to generate a signal indicative of a pressure of port chamber 44. Alternatively, pressure sensor 14 can be adapted to generate a signal indicative of a change in pressure of port chamber 44. In more general terms, then, pressure sensor 14 is any device capable of sensing and signaling information indicative of pressure characteristics associated with port chamber 44 or fluid port assembly 40 more generally. In this regard, pressure sensor 14 can be electronically coupled to detector circuit 50 (FIGS. 1A, 1B) or indicator device 16 (FIGS. 2-4), 60 (FIG. 5) in a variety of manners. For example, electrical wiring (not shown) can provide the desired electrical connection. Alternatively, a wireless link can be provided between pressure sensor 14 and the processing device in question.

Systems 10 as thus described can be used to confirm entry of needle 20 through septum 42 into port chamber 44. Systems 10 may also be used to provide a clinician with sufficient information to make this determination (not shown).

In general terms and without being bound by the following theory, it is believed that insertion of needle 20 through septum 42 typically requires application of a pressure exceeding a minimum threshold. Once the force threshold is met, needle 20 will quickly enter into port chamber 44 due to the dynamic friction force being less than the septum puncture force. Needle 20 will thus rapidly enter port chamber 44 independent of clinical technique because the transit time is typically much less than human response reflex time. Rapid entry of the volume of needle 20 into chamber 44, that generally has a fixed volume, will result in a rapid increase of pressure functionally related to the displacement volume of needle 20. The mechanical energy caused by the increased pressure is stored in mechanisms of elastic compliance that are present within the infusion device 12 or catheter 34. The stored energy will dissipate out of chamber 44 by the mechanism of fluid flow through catheter 34 or reservoir 32 and will eventually return to the ambient level. The events of rapid pressurization followed by the dissipation result in a characteristic pressure profile that can be detected by an electronic circuit or a computer software algorithm to indicate the needle entry event. An inverse pressure profile event occurs during the removal of a needle from a septum.

Figure 10:
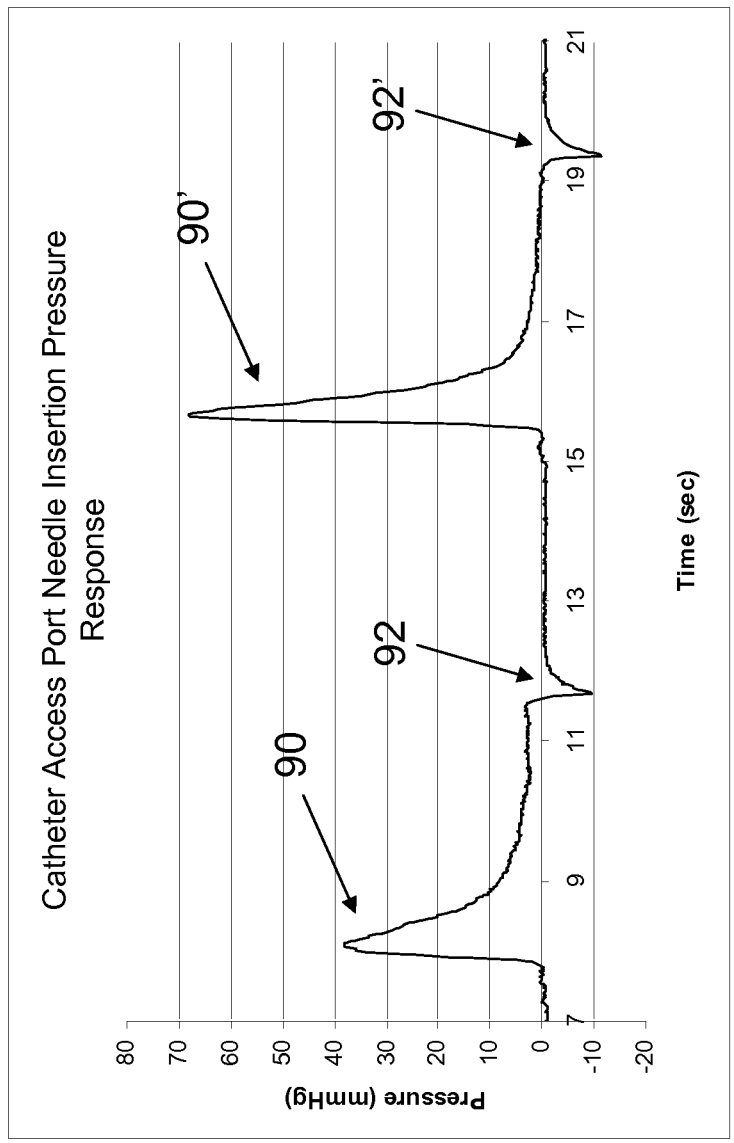
FIG. 10 is a graph of pressure monitored in a chamber of a port assembly of an implantable infusion device over time, showing pressure response to needle insertion into the chamber, and needle withdrawal from the chamber.

Referring to FIG. 10, exemplary transient pressure profiles 90, 90', 92, 92' associated with (i) needle insertion through septum into port chamber (90, 90') and (ii) needle withdrawal from port chamber through septum (92, 92') are shown. The pressure profiles depicted in FIG. 10, were obtained by inserting a needle into a SynchroMed® II pump's catheter access port. The pump was specially fixtured with a Medtronic Chronicle Pressure Sensor (which is a capacitive-based pressure sensor having a Titanium flexible membrane). A short segment of catheter tubing was used to attach the pump's output port to a 1 inch titanium block sensor housing chamber. Data was recorded using a National Instruments® data acquisition system.

Figure 11:
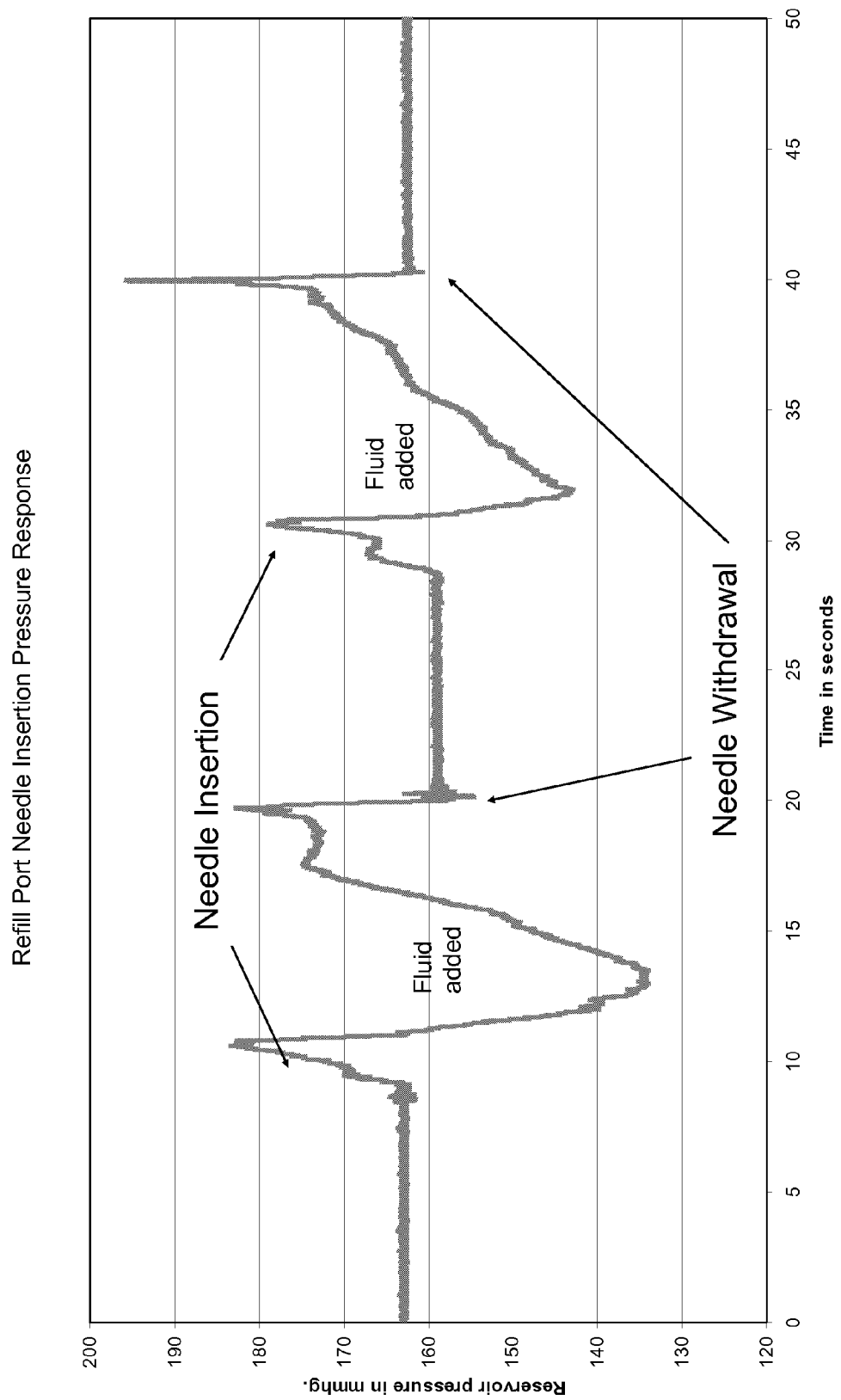
FIG. 11 is a graph of pressure monitored in a chamber of a port assembly of an implantable infusion device over time, showing pressure response to needle insertion into the chamber, needle withdrawal from the chamber, and fluid delivery into the chamber.

Referring to FIG. 11, exemplary pressure profiles associated with insertion of a needle into a refill port chamber, injection of fluid from the needle into the chamber, and needle withdrawal from the chamber are shown. The pressure profiles depicted were obtained by inserting a needle into a SynchroMed® II pump's refill port. The pump was specially fixtured with a Medtronic Chronicle Pressure Sensor. The sensor was fastened to a specially machined pump to a channel that allowed measurement of the pressure of the refill port. Data was recorded using a National Instruments® data acquisition system.

As can be seen from FIGS. 10 and 11, following the insertion of a needle through a septum into a port chamber, a rapid increase in pressure is observed. Within seconds, the pressure in the chamber returns substantially to the pressure observed prior to needle insertion or ambient pressure. As shown in FIG. 11, the same pressure sensor that is used to measure pressure changes associated with needle insertion into the port chamber can be used to measure pressure changes associated with fluid flow in to the port chamber or reservoir in fluid communication with the port chamber. It may be desirable for slight flow restriction between the fill port chamber and the reservoir to be present to allow for pressure increase associated with fluid flow into the port chamber to be more readily identified.

Figure 12:
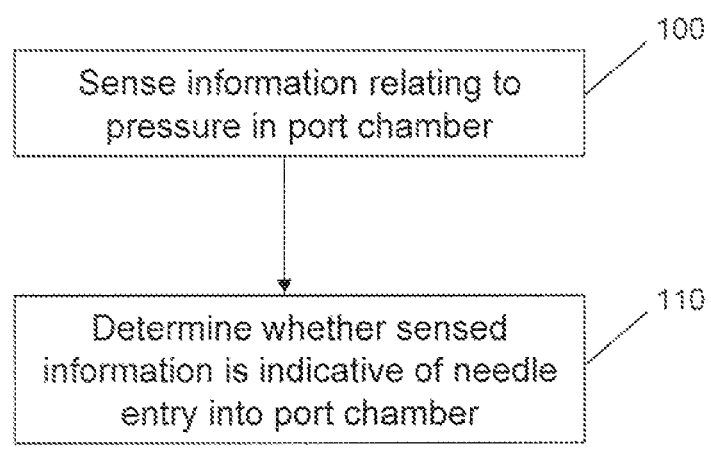
FIGS. 12-15 are flow diagrams of representative methods in accordance with the principles of the teachings herein.

In light of the above, FIG. 12 provides a flow diagram illustrating a method for monitoring needle insertion into a port chamber. The method includes sensing information relating to pressure in a port chamber (100) and determining whether the sensed information is indicative of insertion of a needle through a septum into a port chamber (110). One way to determine whether the sensed information is indicative of insertion of a needle through a septum into a port chamber is to determine whether the sensed information reflects a transient pressure increase in the chamber (e.g., as described with regard to FIGS. 10 and 11). For example, it may be determined whether an increase in chamber pressure is followed by a return to a substantially similar pressure to that prior to the pressure increase within a suitable amount of time to be indicative of needle insertion into the port chamber. A suitable amount of time may be within 5 seconds, within 2 seconds, within 1 second, etc. Alternatively, or in addition, it may be determined whether an increase in pressure is followed by a logarithmic decay profile characteristic of a needle insertion into a port chamber. As the profile of various port assemblies in various infusion devices may vary depending on configuration, device components or materials, or the like, it may be desirable to (i) identify a characteristic transient pressure pattern associated with needle insertion into a port chamber of given device or class of devices and (ii) compare sensed pressure-related information to the characteristic transient pressure pattern to determine whether the sensed information is indicative of needle insertion into the port chamber.

Figure 13:
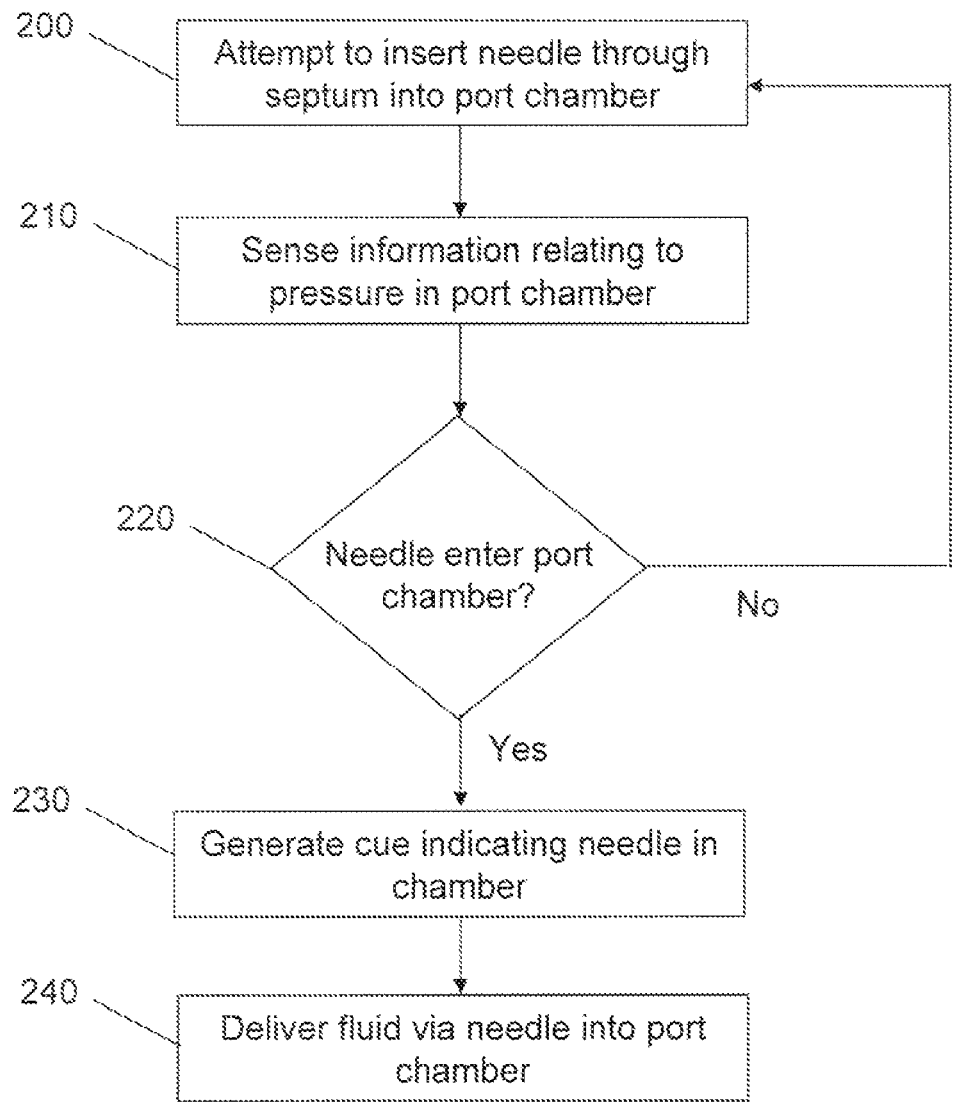

With the above discussion in mind, FIG. 13 provides a flow diagram illustrating a method for monitoring needle insertion into a port chamber. The method includes inserting a needle into a patient in an attempt to access a port chamber of an infusion device (200) and sensing information relating to pressure in the port chamber (210). A determination may then be made as to whether the sensed information is indicative of insertion of the needle through a septum into the port chamber (220). If the sensed information is indicative of needle insertion into the chamber, a cue may be generated to indicate that the needle is in the chamber (230), alerting a clinician of successful placement of the needle. The clinician may then proceed with delivering fluid into the chamber via the needle (240). If the sensed information is not indicative of needle insertion into the chamber, a cue will not be generated and the clinician may then again attempt to insert the needle into the chamber (200).

Figure 14:
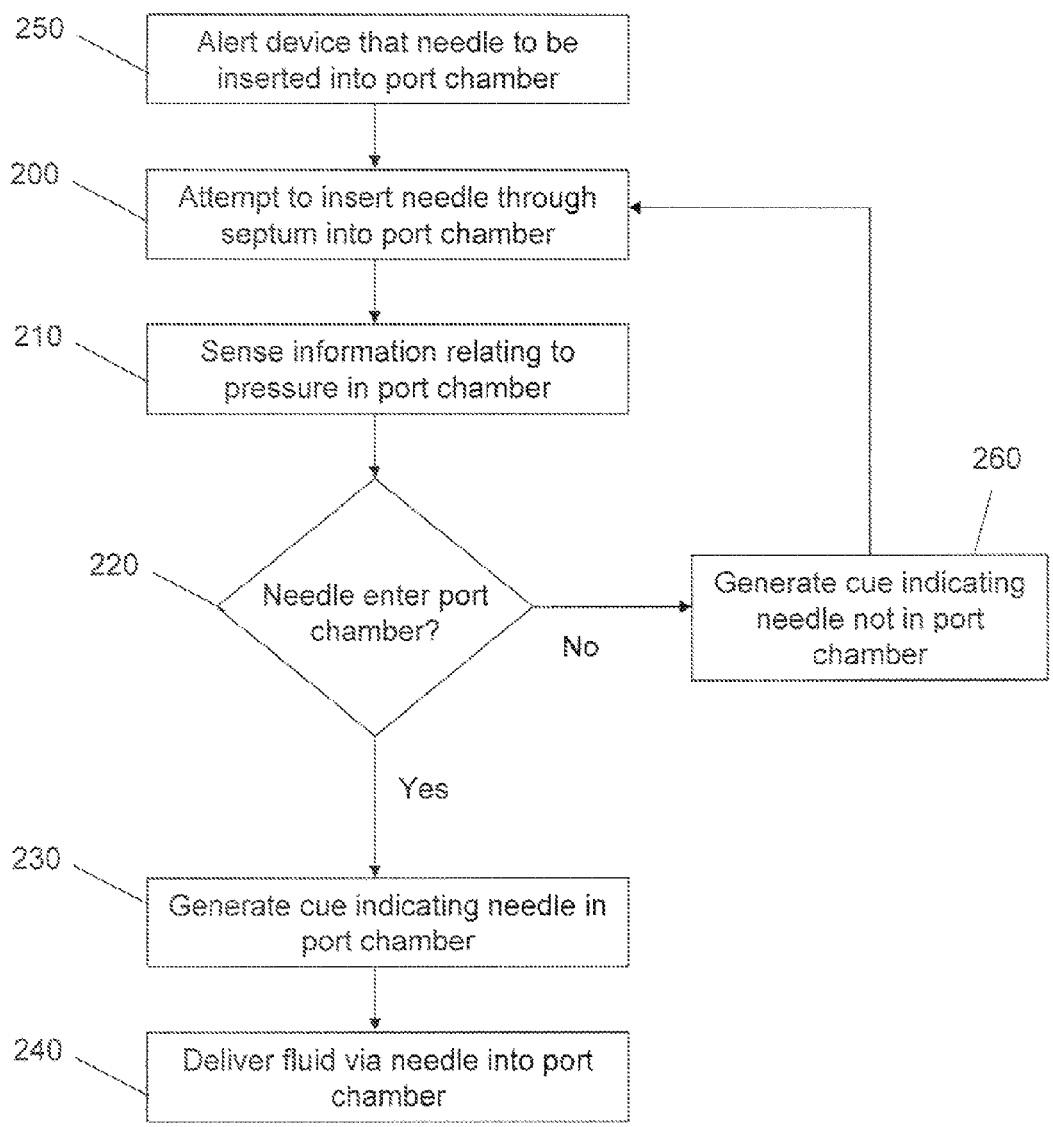

FIG. 14 provides a flow diagram illustrating a method for monitoring needle insertion into a port chamber similar to that shown in FIG. 13. In FIG. 14, the device is first alerted that a needle is about to be inserted into a port chamber (250); e.g., through the use of a programmer device. A clinician may then insert the needle into a patient in an attempt to access the port chamber of the infusion device (200). Information relating to pressure in the port chamber is sensed (210) and a determination is made as to whether the sensed information is indicative of insertion of the needle through a septum into the port chamber (220). If the sensed information is indicative of needle insertion into the chamber, a cue may be generated to indicate that the needle is in the chamber (230), alerting a clinician of successful placement of the needle. The clinician may then proceed with delivering fluid into the chamber via the needle (240). However, if no information indicative of needle entry into port chamber is sensed, a cue may be generated to indicate that the needle is not in the port chamber (260), allowing the clinician, to then again attempt to insert the needle into the chamber (200). Because the device is alerted that a needle is soon to be inserted into a port chamber (250), an actual cue may be generated to alert the physician that no needle has been detected in the port chamber (260); e.g., if no indicative pressure information is sensed with in a predetermined time from alerting the device. Systems capable of carrying out such methods may be desirable as compared to those carrying out a method described in FIG. 13, where the clinician relies on lack of a cue to determine that the needle has not been inserted into the port chamber. The method described in FIG. 14, may also be desirable from a power-savings perspective. That is, it is possible to supply power to pressure sensor, detector circuit, indicator device, etc. only after the device is alerted that a needle is about to be inserted, as opposed to continuously supplying power to such components.

Figure 15:
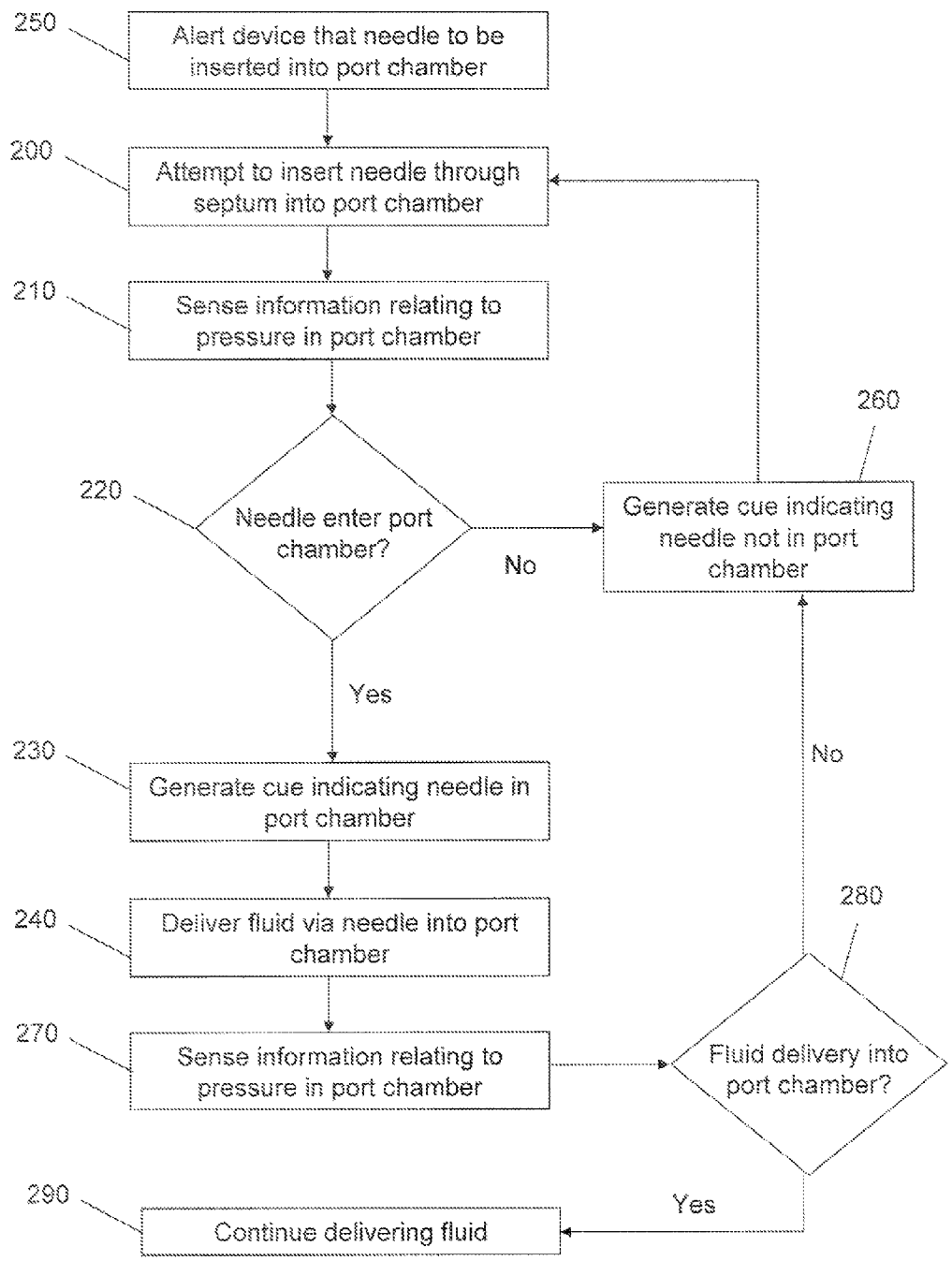

FIG. 15 provides a flow diagram illustrating a method for monitoring needle insertion into a port chamber similar to that shown in FIG. 14. The method illustrated includes sensing information relating to pressure in the port chamber (270) and determining whether the sensed information is indicative of fluid being delivered into the port chamber (280); e.g., a characteristic rise in pressure. If the sensed information is not indicative of fluid being delivered into the port chamber, a cue may be generated indicating that the needle is not in the port chamber (260), alerting the clinician to again attempt to insert the needle into port chamber (200). In the absence of such a cue, the clinician may continue to deliver fluid into the chamber via the needle (290).

One of skill in the art will understand that components or steps described herein regarding a given embodiment or set of embodiments may readily be omitted, substituted, or added from, with, or to components or steps of other embodiments or sets of embodiments, as appropriate or desirable.

What is claimed is:

1. An implantable infusion device comprising:
   a housing;
   a port assembly defining a port chamber, the port assembly including a septum disposed across the chamber to fluidly seal the port chamber relative to an exterior of the housing, the port assembly being disposed in the housing such that the chamber is accessible by a needle inserted through the opening and the septum from the exterior of the housing;

a pressure sensor in fluid communication with the port chamber; and, electronics disposed in the housing and operably coupled to the pressure sensor, the electronics including a computer readable medium containing instructions that when implemented determine whether a transient pressure increase associated with insertion of a needle into the port chamber, prior to dispensing fluid into the port chamber, is detected via the pressure sensor.

2. The device of claim 1, wherein the pressure sensor is operably disposed in the port chamber.

3. The device of claim 1, further comprising a reservoir in fluid communication with the port chamber.

4. The device of claim 1, wherein the pressure sensor is operably disposed in the reservoir.

5. The device of claim 1, wherein the port assembly is a refill port assembly.

6. The device of claim 1, wherein the port assembly is a catheter access port assembly.

7. The device of claim 1, further comprising a telemetry circuit configured to transmit a signal to an external device, wherein the signal indicates whether a needle entry into the port chamber has been detected.

8. The device of claim 1, further comprising an indicator circuit, wherein the indicator circuit is configured to generate a sensory cue indicative of detection of needle entry into the port chamber.

9. The device of claim 1, wherein the electronics are configured to determine whether the sensed pressure change is indicative of insertion of the needle through the septum into the port chamber, prior to dispensing fluid into the port chamber, by determining whether the sensed pressure change reflects a transient pressure increase in the chamber.

10. The device of claim 9, wherein determining whether the sensed pressure change is indicative of insertion of the needle through the septum into the port chamber further comprises determining whether the pressure in the chamber returns, within 5 seconds, to a level substantially similar to that prior to the transient pressure increase.

11. The device of claim 9, wherein determining whether the sensed pressure change is indicative of insertion of the needle through the septum into the port chamber further comprises determining whether the pressure in the chamber returns, within 2 seconds, to a level substantially similar to that prior to the transient pressure increase.

12. The device of claim 9, wherein determining whether the sensed pressure change is indicative of insertion of the needle through the septum into the port chamber further comprises determining whether the pressure in the chamber returns, in a logarithmic decay profile over time, to a level substantially similar to that prior to the transient pressure increase.

* * * * *